US012076187B2

(12) United States Patent
Morimoto et al.

(10) Patent No.: US 12,076,187 B2
(45) Date of Patent: Sep. 3, 2024

(54) ULTRASONIC ENDOSCOPE AND MANUFACTURING METHOD OF ULTRASONIC ENDOSCOPE

(71) Applicant: FUJIFILM Corporation, Tokyo (JP)

(72) Inventors: Yasuhiko Morimoto, Kanagawa (JP); Tsuneo Fukuzawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 154 days.

(21) Appl. No.: 16/905,873

(22) Filed: Jun. 18, 2020

(65) Prior Publication Data

US 2020/0315575 A1 Oct. 8, 2020

Related U.S. Application Data

(63) Continuation of application No. PCT/JP2018/047061, filed on Dec. 20, 2018.

(30) Foreign Application Priority Data

Jan. 29, 2018 (JP) ................................ 2018-012782

(51) Int. Cl.
*A61B 8/00* (2006.01)
*A61B 1/015* (2006.01)
(Continued)

(52) U.S. Cl.
CPC ............... *A61B 8/445* (2013.01); *A61B 8/12* (2013.01); *A61B 1/015* (2013.01); *A61B 1/018* (2013.01); *A61B 2562/12* (2013.01)

(58) Field of Classification Search
CPC ........... A61B 8/445; A61B 8/12; A61B 1/015; A61B 1/018; A61B 2562/12;
(Continued)

(56) References Cited

U.S. PATENT DOCUMENTS 5,474,074 A * 12/1995 Suorsa .................... A61B 8/12
                                                          29/25.35
6,241,744 B1 * 6/2001 Imran ................... A61B 8/0833
                                                        606/167
(Continued)

FOREIGN PATENT DOCUMENTS

| CN | 103269645 | 8/2013 |
| CN | 104619265 | 5/2015 |
(Continued)

OTHER PUBLICATIONS

"International Search Report (Form PCT/ISA/210) of PCT/JP2018/047061," mailed on Mar. 12, 2019, with English translation thereof, pp. 1-5.
(Continued)

*Primary Examiner* — Pascal M Bui Pho
*Assistant Examiner* — Michael Yiming Fang
(74) *Attorney, Agent, or Firm* — JCIPRNET

(57) ABSTRACT

There is provided an ultrasonic endoscope, in which bending of a signal cable at a time of assembling a distal end portion is alleviated and the signal cable is prevented from being disconnected, and a manufacturing method thereof. An ultrasonic endoscope (1) includes a cable insertion hole (88), a storing portion (90) that is formed on a distal end side of the cable insertion hole (88), an ultrasonic transducer (50) that has an ultrasonic vibrator disposed in the storing portion (90), an elevator housing portion (62) that is open in a first direction, an elevator (60), and a distal end portion main body (36) that has a signal cable (86) connected to the ultrasonic vibrator, in which the storing portion (90) is disposed at a position offset in a second direction orthogonal to a first direction from a position where the cable insertion hole (88) is provided, the storing portion (90) has a cable introducing portion (92) that introduces the signal cable (86) into the cable insertion hole (88), and the cable introducing
(Continued)

portion (92) has a guiding surface (94) in which a width of the storing portion (90) in the second direction gradually increases toward a proximal end side, and a manufacturing method thereof.

13 Claims, 13 Drawing Sheets

(51) Int. Cl.
*A61B 1/018* (2006.01)
*A61B 8/12* (2006.01)

(58) Field of Classification Search
CPC ... A61B 8/0841; A61B 8/4483; A61B 8/4494; A61B 8/00; A61B 1/00
See application file for complete search history.

(56) References Cited

U.S. PATENT DOCUMENTS

| | | | |
|---|---|---|---|
| 7,771,349 B2 | 8/2010 | Kohno | |
| 10,772,605 B2 | 9/2020 | Morimoto | |
| 2001/0041841 A1 | 11/2001 | Ohara et al. | |
| 2004/0082883 A1* | 4/2004 | Kohno | A61B 1/00177 601/2 |
| 2007/0266792 A1* | 11/2007 | Oosawa | A61B 8/4488 73/661 |
| 2011/0301413 A1* | 12/2011 | Morimoto | A61B 1/00087 600/104 |
| 2013/0158410 A1* | 6/2013 | Ohgishi | A61B 8/12 600/462 |
| 2014/0058269 A1 | 2/2014 | Rie | |
| 2015/0011891 A1* | 1/2015 | Yamada | A61B 8/4494 600/459 |
| 2015/0173711 A1* | 6/2015 | Hiraoka | A61B 1/0005 600/466 |
| 2016/0183914 A1 | 6/2016 | Fujimura | |
| 2017/0128044 A1 | 5/2017 | Morimoto | |

FOREIGN PATENT DOCUMENTS

| | | | |
|---|---|---|---|
| CN | 106859703 | 6/2017 | |
| JP | H06169982 | 6/1994 | |
| JP | 2000014635 | 1/2000 | |
| JP | 2001104311 | 4/2001 | |
| JP | 2002336257 | 11/2002 | |
| JP | 3709325 B2 * | 10/2005 | |
| JP | 2005287593 | 10/2005 | |
| JP | 2007252457 A * | 10/2007 | ........... A61B 1/0008 |
| JP | 4652518 B2 * | 3/2011 | |
| JP | 2014033716 | 2/2014 | |
| JP | 2017086458 | 5/2017 | |
| WO | 2013035374 | 3/2013 | |
| WO | 2014034191 | 3/2014 | |
| WO | 2014038638 | 3/2014 | |
| WO | 2015053044 | 4/2015 | |

OTHER PUBLICATIONS

"Written Opinion of the International Searching Authority (Form PCT/ISA/237) of PCT/JP2018/047061," mailed on Mar. 12, 2019, with English translation thereof, pp. 1-9.
"Office Action of China Counterpart Application", issued on Nov. 3, 2022, with English translation thereof, pp. 1-24.
"Office Action of China Counterpart Application", issued on Jan. 31, 2023, with English translation thereof, p. 1-p. 23.

* cited by examiner

ULTRASONIC ENDOSCOPE AND MANUFACTURING METHOD OF ULTRASONIC ENDOSCOPE

CROSS-REFERENCE TO RELATED APPLICATIONS

The present application is a Continuation of PCT International Application No. PCT/JP2018/047061 filed on Dec. 20, 2018 claiming priority under 35 U.S.C § 119(a) to Japanese Patent Application No. 2018-012782 filed on Jan. 29, 2018. Each of the above applications is hereby expressly incorporated by reference, in its entirety, into the present application.

BACKGROUND OF THE INVENTION

1. Field of the Invention

The present invention relates to an ultrasonic endoscope, and particularly to an ultrasonic endoscope comprising an ultrasonic transducer in a distal end portion main body of an insertion part and a manufacturing method of an ultrasonic endoscope.

2. Description of the Related Art

In the related art, there is known an ultrasonic endoscope comprising an elevator and an elevator housing portion, which are in a distal end portion main body of an insertion part to be inserted into a body cavity. A treatment tool that is inserted into a treatment tool insertion channel to be led out from a treatment tool lead-out portion of the distal end portion main body is elevated by the elevator, and a lead-out direction in which the treatment tool is led out can be adjusted by changing an elevation angle of the elevator.

For example, JP2005-287593A and JP2017-086458A disclose an endoscope in which an elevator is provided at a treatment tool lead-out portion, an elevating lever is connected to the elevator via a rotation shaft, an operation wire is connected to the elevating lever, and the operation wire is pushed and pulled through operation of an operation part.

SUMMARY OF THE INVENTION

However, since an observation unit is provided on the side of the elevator (treatment tool lead-out portion) in the endoscope described in JP2005-287593A, the treatment tool comes into an observation field of view from a peripheral portion of a monitor screen in a case where the treatment tool is led out. For this reason, the precision of the treatment tool at a spot where a puncture needle or a stent is to be penetrated has been reduced. In order to reduce a blind area where the treatment tool led out from the treatment tool lead-out portion does not come into the field of view of the observation window, a position of each member in a distal end portion main body has been examined.

As disclosed in JP2017-86458A, a signal cable connected to an ultrasonic vibrator is inserted into a wiring insertion hole provided below the elevator along a longitudinal axis of a distal end portion. In a case where the position of the member is changed to secure the observation field of view, the signal cable bends and causes disconnection in some cases depending on positions of the ultrasonic vibrator and the signal cable, and the disposition of the member is limited.

The present invention is devised in view of such circumstances, and an object thereof is to provide an ultrasonic endoscope in which bending of a signal cable at the time of assembling a distal end portion of the ultrasonic endoscope is alleviated and the signal cable is prevented from being disconnected. In addition, another object thereof is to provide a manufacturing method of an ultrasonic endoscope, in which assemblability of an ultrasonic transducer into the distal end portion main body is improved.

According to an aspect of the present invention, in order to achieve the object of the present invention, there is provided an ultrasonic endoscope comprising a distal end portion main body that is provided at a distal end of an insertion part and has a cable insertion hole therein, a storing portion that is provided in the distal end portion main body and is formed on a distal end side in an axial direction of the distal end portion main body from the cable insertion hole, an ultrasonic transducer that is disposed in the storing portion and has a plurality of ultrasonic vibrators, an elevator housing portion that is provided in the distal end portion main body and is open in a first direction orthogonal to the axial direction of the distal end portion main body, an elevator that is provided in the elevator housing portion and is rotatably supported, and a plurality of signal cables that are connected to the plurality of ultrasonic vibrators, respectively. The storing portion is disposed at a position offset in a second direction that is orthogonal to the axial direction of the distal end portion main body and is orthogonal to the first direction from a position where the cable insertion hole is provided. The storing portion has a cable introducing portion that introduces the plurality of signal cables into the cable insertion hole. The cable introducing portion has a guiding surface in which a width of the storing portion in the second direction gradually increases toward a proximal end side in the axial direction of the distal end portion main body.

According to the aspect of the present invention, it is preferable that the distal end portion main body has a needle insertion hole that guides a needle for injecting a filler to the storing portion.

According to the aspect of the present invention, when the needle insertion hole is projected on a plane orthogonal to the axial direction of the distal end portion main body, it is preferable that the needle insertion hole is disposed at a position closer to the storing portion than the cable insertion hole is.

According to the aspect of the present invention, it is preferable that the needle insertion hole and the cable insertion hole communicate with each other via a gap.

According to the aspect of the present invention, it is preferable that the guiding surface is formed by an inclined surface which is obliquely inclined with respect to the axial direction of the distal end portion main body.

According to the aspect of the present invention, when the cable insertion hole and the elevator housing portion are projected on a plane perpendicular to the first direction, it is preferable that the cable insertion hole is disposed in a region different from the elevator housing portion.

According to the aspect of the present invention, it is preferable that when the distal end portion main body is projected on a plane orthogonal to the axial direction of the distal end portion main body the distal end portion main body has an observation window of which a position in the first direction is disposed on an opening side of the elevator housing portion.

According to the aspect of the present invention, it is preferable that the observation window is disposed on the proximal end side in the axial direction of the distal end portion main body from the elevator housing portion.

According to the aspect of the present invention, it is preferable that the observation window is disposed to be offset from the elevator housing portion in the second direction.

According to another aspect of the present invention, in order to achieve the object of the present invention, there is provided a manufacturing method of an ultrasonic endoscope comprising a distal end portion main body that is provided at a distal end of an insertion part and has a cable insertion hole therein, a storing portion that is provided in the distal end portion main body and is formed on a distal end side in an axial direction of the distal end portion main body from the cable insertion hole, an ultrasonic transducer that is disposed in the storing portion and has a plurality of ultrasonic vibrators, an elevator housing portion that is provided in the distal end portion main body and is open in a first direction orthogonal to the axial direction of the distal end portion main body, an elevator that is provided in the elevator housing portion and is rotatably supported, and a plurality of signal cables that are connected to the plurality of ultrasonic vibrators, respectively, in which the storing portion is disposed at a position offset in a second direction that is orthogonal to the axial direction of the distal end portion main body and is orthogonal to the first direction from a position where the cable insertion hole is provided, the storing portion has a cable introducing portion that introduces the plurality of signal cables into the cable insertion hole, and the cable introducing portion has a guiding surface in which a width of the storing portion in the second direction gradually increases toward a proximal end side in the axial direction of the distal end portion main body. The manufacturing method comprises a step of inserting the plurality of signal cables into the cable insertion hole from the distal end side to the proximal end side in the axial direction of the distal end portion main body through the cable introducing portion, a step of storing the plurality of ultrasonic vibrators in the storing portion, and a step of filling a gap between the ultrasonic vibrator and the storing portion and a gap between the signal cables and the cable insertion hole with a filler.

According to the aspect of the present invention, it is preferable that the distal end portion main body has a needle insertion hole that communicates with the cable insertion hole via a gap and guides a needle for injecting the filler to the storing portion. In the step of filling the gap with the filler, it is preferable that the needle is inserted from the proximal end side of the needle insertion hole in the axial direction of the distal end portion main body, and the filler is injected from the distal end side in the axial direction of the distal end portion main body.

In the ultrasonic endoscope of the present invention, the abrupt bending of the signal cables can be suppressed as the signal cables are introduced into the cable insertion hole along the guiding surface from the storing portion where the ultrasonic transducer is disposed. Therefore, the signal cables are prevented from being disconnected. In addition, as the signal cables are introduced into the cable insertion hole along the guiding surface, the signal cables can be introduced smoothly, and the assemblability of the ultrasonic transducer into the distal end portion main body can be improved.

DESCRIPTION OF THE PREFERRED EMBODIMENTS

Hereinafter, an ultrasonic endoscope and a manufacturing method of an ultrasonic endoscope according to a preferable embodiment of the present invention will be described with reference to the accompanying drawings.

(Ultrasonic Endoscope)

Figure 1:
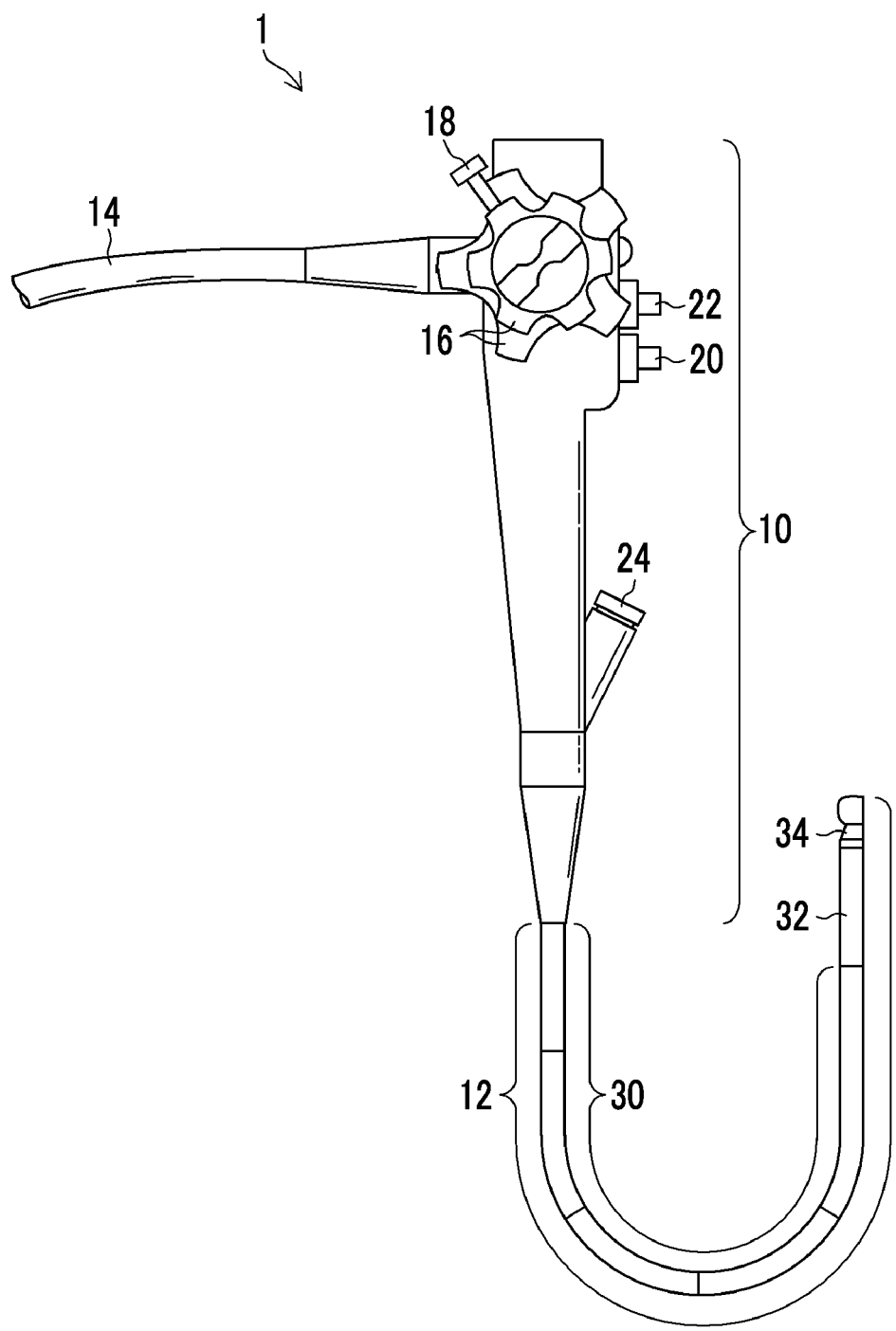
FIG. 1 is an overall view of an ultrasonic endoscope according to the embodiment of the present invention.

FIG. 1 is an overall view of an ultrasonic endoscope 1 to which the present invention is applied.

The ultrasonic endoscope 1 (hereinafter, also simply referred to as the "endoscope 1") illustrated in FIG. 1 is configured by an operation part 10 that is gripped by a surgeon to perform various types of operation, an insertion part 12 that is inserted into a body cavity of a patient, and a universal cord 14. The endoscope 1 is connected to system configuring devices such as a processor device and a light source device (not illustrated) that configure an endoscope system via the universal cord 14.

The operation part 10 is provided with various types of operation members operated by a surgeon, for example, an angle knob 16, an elevating operation lever 18, an air supply and water supply button 20, and a suction button 22, of which workings will be described later as appropriate.

In addition, the operation part 10 is provided with a treatment tool inlet 24 through which a treatment tool is inserted into a treatment tool insertion channel inserted in the insertion part 12.

The insertion part 12 extends from a distal end of the operation part 10 and is formed to have a small diameter and an elongated shape as a whole.

In addition, the insertion part 12 is configured by a flexible portion 30, a curving portion 32, and a distal end portion 34 in order from a proximal end side to a distal end side.

The flexible portion 30 occupies most of the insertion part 12 from the proximal end side, and has flexibility allowing to be curved in any direction. In a case where the insertion part 12 is inserted in the body cavity, the flexible portion 30 curves along an insertion passage into the body cavity.

The curving portion 32 curves in an up-and-down direction and a right-and-left direction through rotating operation of the angle knob 16 of the operation part 10. The distal end portion 34 can be directed in a desired direction as the curving portion 32 curves.

As will be described in detail later with reference to FIGS. 2 to 4, the distal end portion 34 is configured by a distal end portion main body 36, and comprises an ultrasonic transducer 50 having a plurality of ultrasonic vibrators, an elevator housing portion 62, and an elevator 60 that is provided in the elevator housing portion 62. In addition, the elevator housing portion 62 has an opening portion 58 that is open in a first direction perpendicular to a direction of an axis 38 of the distal end portion main body 36. Further, the distal end portion main body 36 is provided with a treatment tool outlet 80, which communicates with an inside of the elevator housing portion 62 and through which the treatment tool is led out. The axis 38 of the distal end portion main body 36 refers to a line that matches or is parallel to an axis in a longitudinal direction of the insertion part 12 of FIG. 1.

The universal cord 14 illustrated in FIG. 1 includes an electric cable, a light guide, and a fluid tube therein. The universal cord 14 comprises a connector at an end portion (not illustrated) thereof. Power, a control signal, illumination light, a liquid, and a gas, which are necessary for operating the endoscope 1, are supplied from the system configuring device to the endoscope 1 by the connector being connected to a predetermined system configuring device that configures the endoscope system, such as a processor device and a light source device. In addition, data of an observation image acquired by an image pick-up unit and data of an ultrasound image acquired by the ultrasonic transducer are transmitted from the endoscope 1 to the system configuring device. The observation image and the ultrasound image, which are transmitted to the system configuring device, can be displayed on a monitor and can be observed by a surgeon.

(Configuration of Distal End Portion)

Next, a configuration of the distal end portion 34 of the insertion part 12 will be described. FIG. 2 is a perspective view illustrating the appearance of the distal end portion 34. FIG. 3 is a plan view (top view). FIG. 4 is a side cross-sectional view of the distal end portion main body taken along line 4-4 in FIG. 3. FIG. 5 is a side cross-sectional view of the distal end portion main body taken along line 5-5 in FIG. 3.

The distal end portion 34 has the distal end portion main body 36 forming an outer wall and an internal partition wall thereof. The distal end portion main body 36 is formed of an insulating material having an insulating property, for example, a resin material such as a methacrylic resin and a plastic including polycarbonate. The ultrasonic transducer 50 having the plurality of ultrasonic vibrators is disposed in a storing portion (shown with a reference "90" in FIG. 7) provided on the distal end side of the distal end portion main body 36.

As illustrated in FIGS. 2 to 5, the distal end portion main body 36 is configured by a base portion 40, in which an observation window 44, illumination windows 46L and 46R, and the elevator housing portion 62 are formed, and an extension portion 42 extending from the base portion 40 to the distal end side. The convex ultrasonic transducer 50 is disposed in the extension portion 42. The ultrasonic transducer 50 has the plurality of ultrasonic vibrators that transmit and receive ultrasonic waves, and has an ultrasonic wave transmitting and receiving surface 52 formed by arranging the respective ultrasonic vibrators in a curved shape along the direction of the axis 38 of the distal end portion main body 36. The ultrasonic transducer 50 acquires data for generating an ultrasound image of a body tissue.

Figure 2:
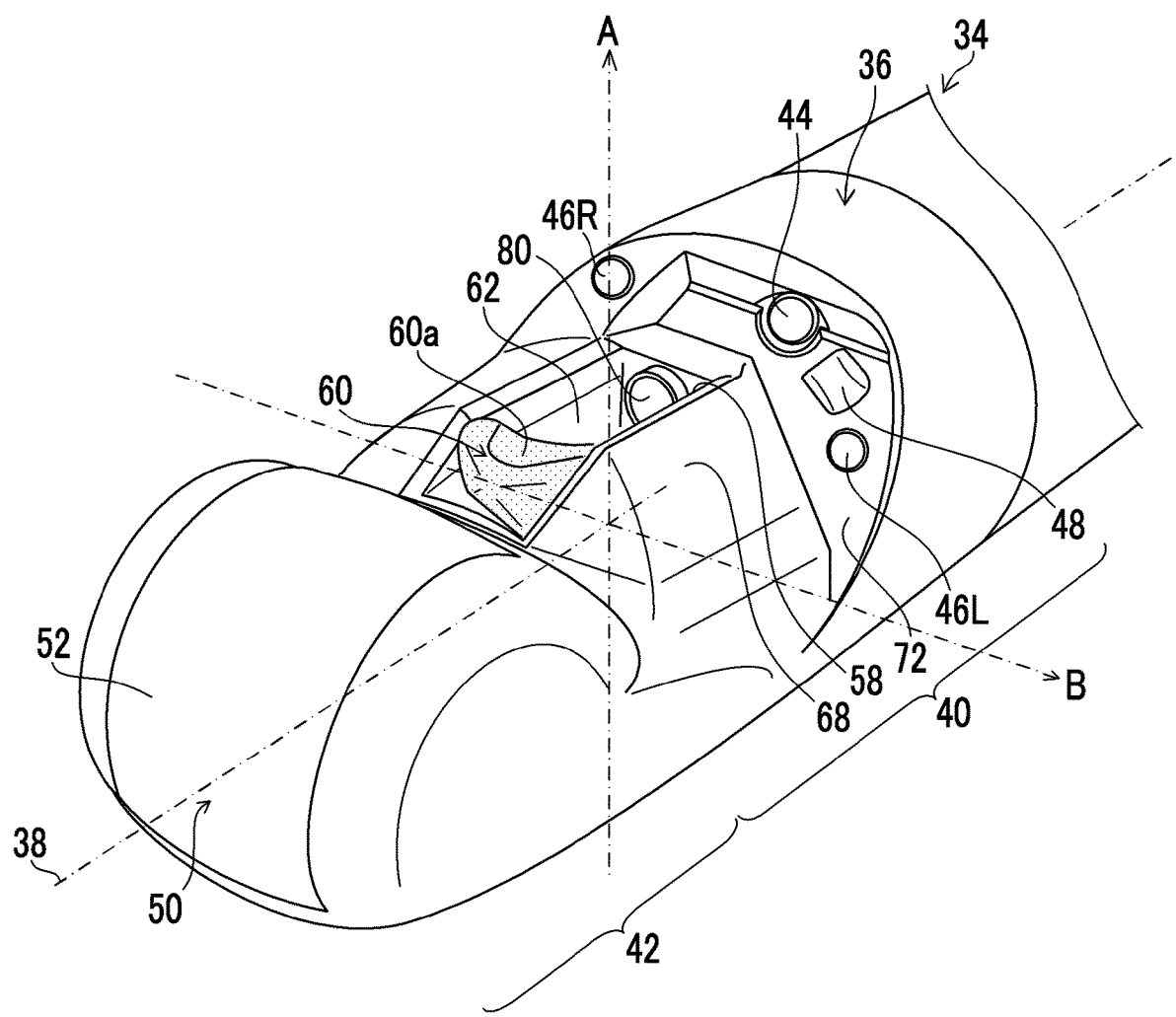
FIG. 2 is a perspective view illustrating an appearance of a distal end portion of an insertion part.
Figure 3:
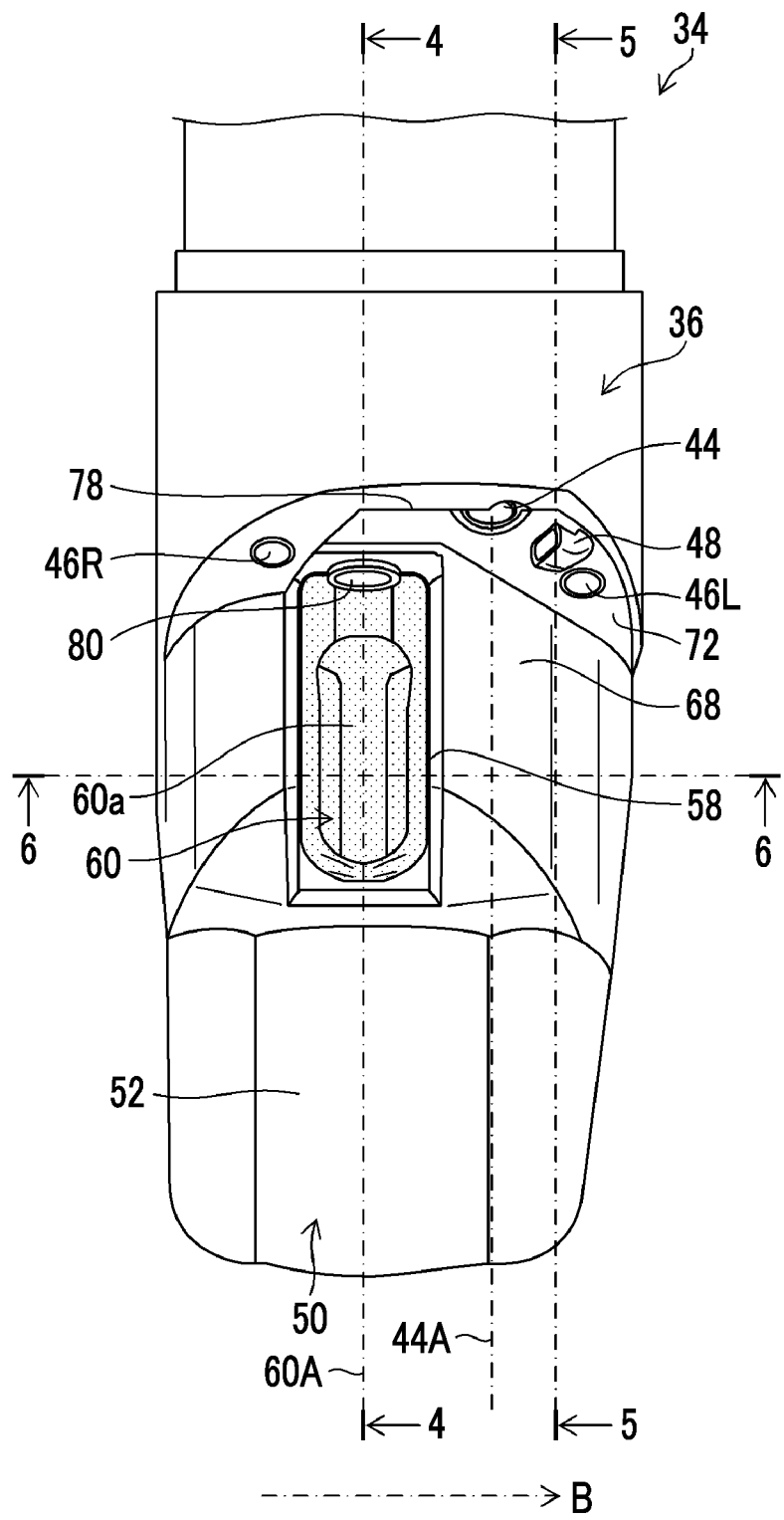
FIG. 3 is a plan view (top view) illustrating the appearance of the distal end portion of the insertion part.

As illustrated in FIGS. 2 and 3, the distal end portion main body 36 is provided with the observation window 44, the illumination windows 46L and 46R, an air supply and water supply nozzle 48, the opening portion 58 through which the treatment tool is led out, and a standing wall portion 68 provided around the opening portion 58.

The opening portion 58 is provided in the base portion 40 of the distal end portion main body 36. The treatment tool is led out from the opening portion 58 into an ultrasound scanning range of the ultrasonic transducer 50. The opening portion 58 of the elevator housing portion 62 provided in the distal end portion main body 36 is formed to be open in the first direction orthogonal to the direction of the axis 38 of the distal end portion main body 36. In the present specification, the "first direction" is a direction, which is perpendicular to the direction of the axis 38 of the distal end portion main body 36 and in which the opening portion 58 of the elevator housing portion 62 is formed, as shown with an arrow A of FIG. 4. In addition, as illustrated in FIG. 2, a "second direction" refers to a direction shown with an arrow B, which is perpendicular to the direction of the axis 38 of the distal end portion main body 36 and the first direction shown with the arrow A. In addition, "one side in the first direction" refers to a side where the opening portion 58 is open. In addition, in the present specification, the one side in the first direction will be referred to as "up" and "upward", and the other side in the first direction will be referred to as "down" and "downward" in some cases.

The treatment tool is inserted from the treatment tool inlet 24 of the operation part 10 illustrated in FIG. 1 to the insertion part 12.

Figure 4:
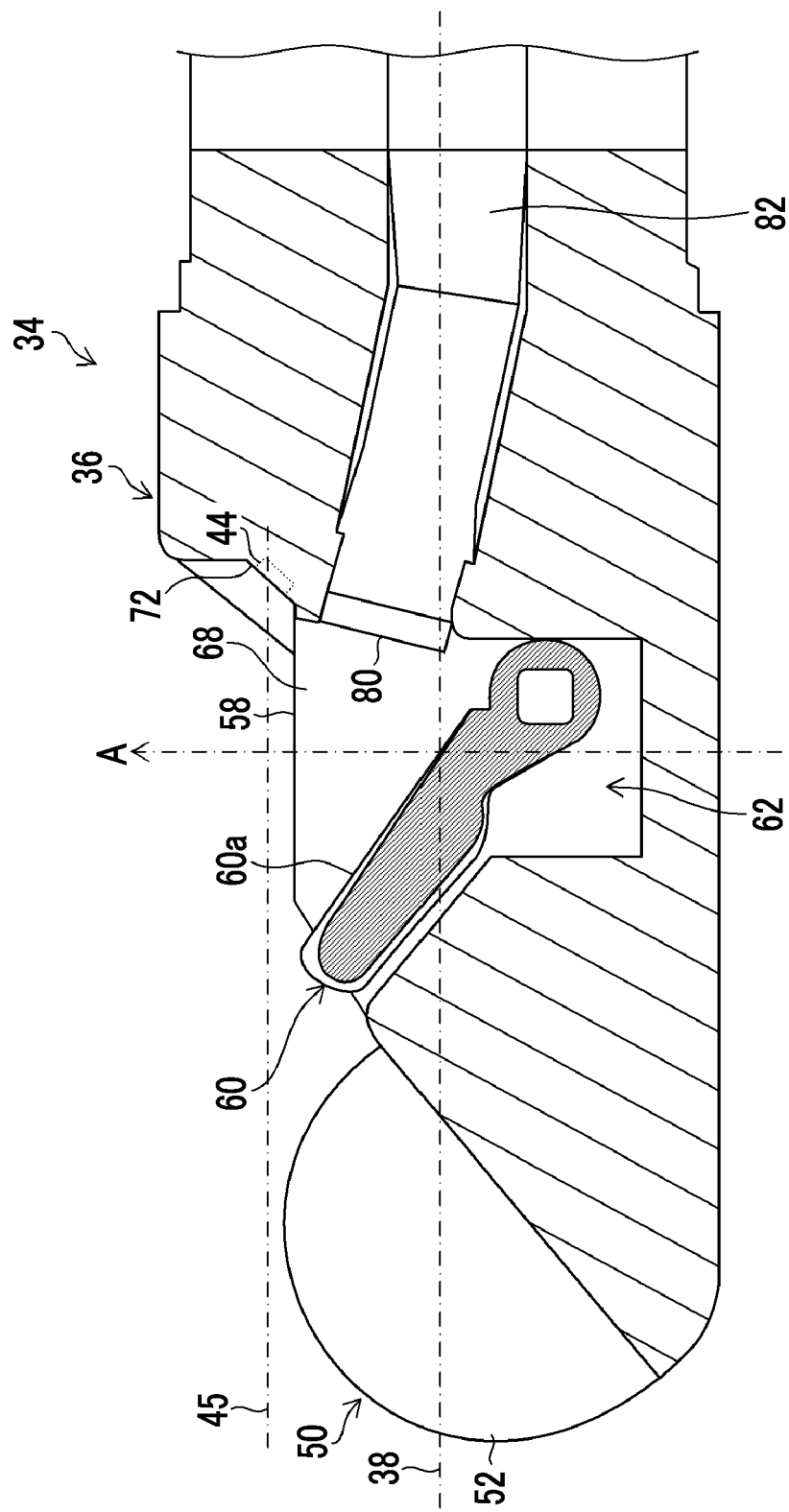
FIG. 4 is a side cross-sectional view illustrating the distal end portion of the insertion part.
Figure 5:
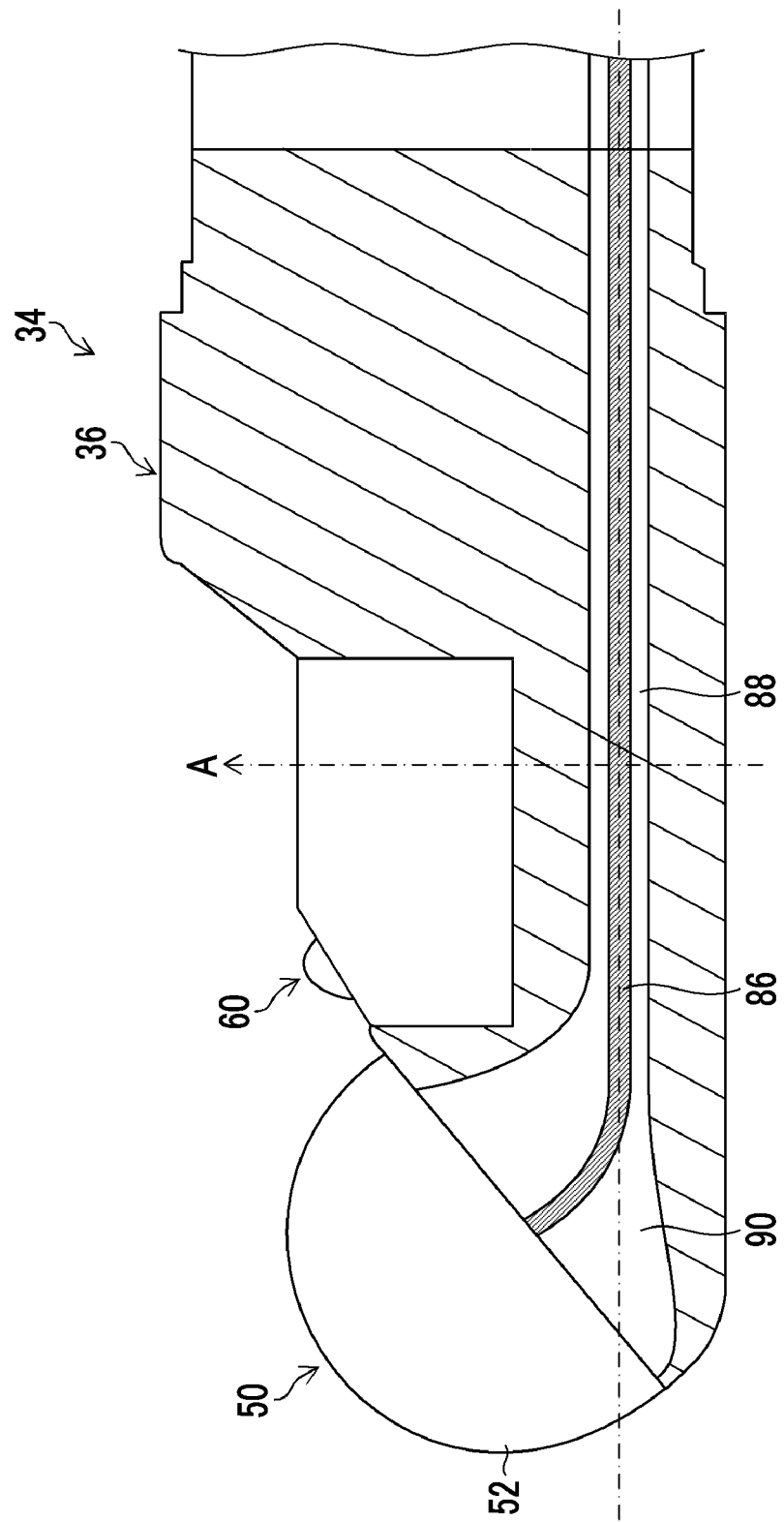
FIG. 5 is a cross-sectional view taken along line 5-5 in FIG. 3.

As illustrated in FIG. 4, the treatment tool outlet 80 is disposed on the proximal end side of the elevator housing portion 62. The treatment tool outlet 80 communicates with the treatment tool inlet 24 of the operation part 10 (refer to FIG. 1) via a treatment tool insertion channel 82 inserted in the insertion part 12. Accordingly, the treatment tool inserted from the treatment tool inlet 24 is led out from the treatment tool outlet 80 (refer to FIG. 4) to the elevator housing portion 62.

The elevator 60 is disposed to be rotatably supported at a position of the elevator housing portion 62 in front of the treatment tool outlet 80. The elevator 60 is formed of a metal material such as stainless steel, and has a concave guide surface 60a on an upper surface side, which curves upward from the proximal end side to the distal end side of the distal end portion main body 36. The treatment tool, which is led out from the treatment tool outlet 80, is curved upward with respect to the direction of the axis 38 of the distal end portion main body 36 (for example, a longitudinal axis direction of the insertion part 12) along the guide surface 60a, and is led out to the outside from the opening portion 58 above the elevator housing portion 62.

In addition, through the operation of the elevating operation lever 18 illustrated in FIG. 1, the elevator 60 rotates about a rotation shaft and performs an elevating operation. By causing the elevator 60 to perform an elevating operation to adjust an elevation angle from a fallen state, a lead-out direction in which the treatment tool is led out from the opening portion 58 (lead-out angle) can be changed.

The treatment tool insertion channel 82 illustrated in FIG. 4 is also connected to a suction channel (not illustrated), and can also suck a body fluid from the opening portion 58 as the suction button 22 of FIG. 1 is operated.

The observation window 44 is arranged in an observation means forming surface 72 provided on the proximal end side of the elevator housing portion 62. Inside the observation window 44, an imaging system unit, in which an imaging optical system and a solid image pickup element, which configure an image pickup unit, are integrally assembled, is housed. Accordingly, in a case where light from a treatment unit, which is in a field of view of the image pick-up unit, enters from the observation window 44, the light is formed as an observation image on an individual imaging element via the imaging optical system. That is, an image of the treatment unit is picked up by the solid image pickup element.

The observation means forming surface 72, in which the observation window 44 is disposed, is configured by a surface having a normal component toward the distal end side in the direction of the axis 38 of the distal end portion main body 36. That is, the observation means forming surface 72 is formed as an inclined surface, which is inclined upward toward the proximal end side of the distal end portion 34. As the observation means forming surface 72 is set as a surface having the normal component toward the distal end side and the observation means forming surface 72 is provided with the observation window 44, the observation window 44 allows a position where the treatment tool is led out from the opening portion 58 to be in a field of view of the observation window 44. Therefore, the treatment tool from the opening portion 58 to a target treatment position can be checked through the observation window 44. The observation means forming surface 72 may be configured by a vertical surface perpendicular to the direction of the axis 38 of the distal end portion main body 36.

The illumination windows 46L and 46R are provided in the observation means forming surface 72 on both sides with the observation window 44 interposed therebetween. A light emission unit configuring an illumination unit is housed inside the illumination windows 46L and 46R. Illumination light transmitted from the light source device connected to the universal cord 14 via the light guide is emitted from the light emission unit, and the illumination light is emitted to the treatment unit in the field of view of the image pick-up unit via the illumination windows 46L and 46R.

The air supply and water supply nozzle 48 is provided in the observation means forming surface 72. Through operation of the air supply and water supply button 20 of FIG. 1, a cleaning liquid, water, or air (hereinafter, also referred to as the "cleaning liquid or the like") is jetted from the air supply and water supply nozzle 48 to the observation window 44 of FIG. 2, thereby cleaning the observation window 44.

Figure 6:
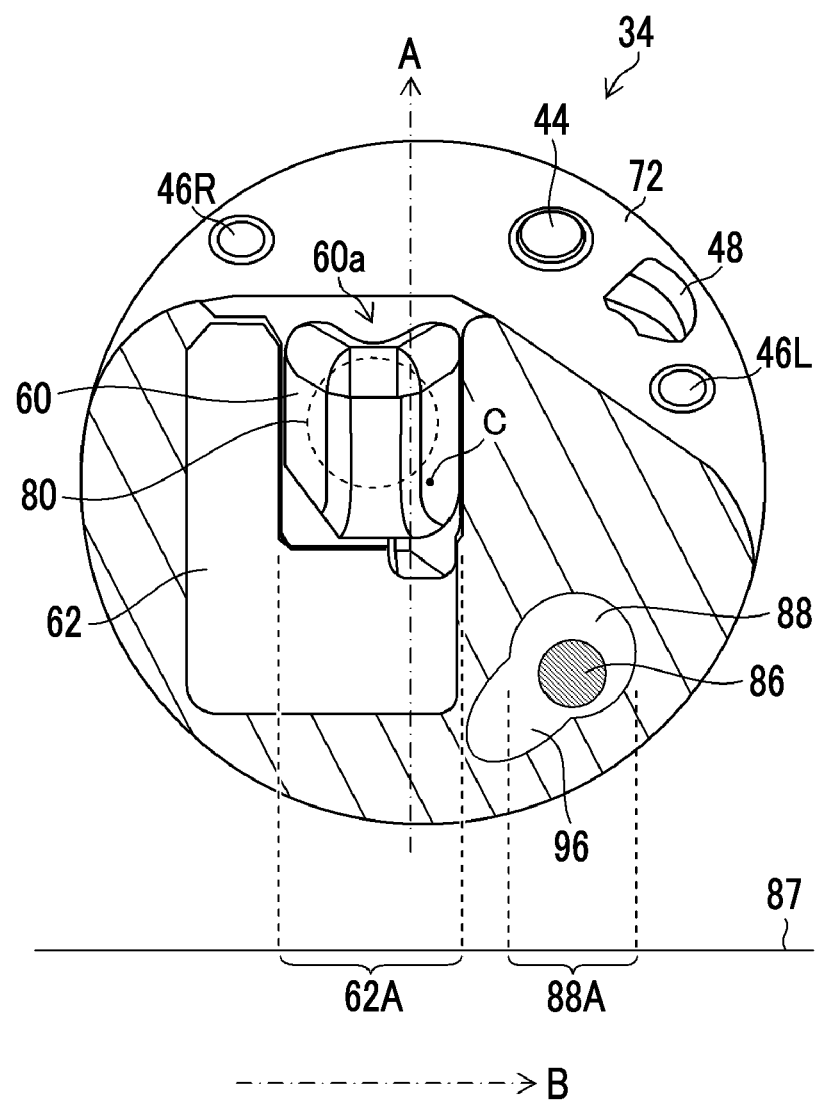
FIG. 6 is a cross-sectional view taken along line 6-6 in FIG. 3.

FIG. 6 is a cross-sectional view taken along line 6-6 in FIG. 3, which is seen from the distal end side of the distal end portion main body 36. The distal end portion main body 36 has a cable insertion hole 88 into which the signal cable 86 is inserted. The signal cable 86 is a cable that connects the ultrasonic vibrators (not illustrated) of the ultrasonic transducer 50 illustrated in FIG. 2 to the system configuring devices. The signal cable 86 is arranged from the insertion part 12 to the universal cord 14 of FIG. 1. The cable insertion hole 88 is provided along the axial direction of the distal end portion main body 36 as illustrated in FIG. 5. In addition, as illustrated in FIG. 6, when the cable insertion hole 88 and the elevator housing portion 62 are projected on an imaginary plane 87 perpendicular to the first direction shown with the arrow A, the cable insertion hole 88 is disposed in a region 88A that is different from a region 62A of the elevator housing portion 62. That is, as illustrated in FIG. 6, the cable insertion hole 88 is disposed on one side of the elevator housing portion 62 in the second direction (the right of the elevator housing portion 62 in FIG. 6). At this time, the elevator housing portion 62 is disposed on the other side in the second direction (the left from a center position C in FIG. 6) to be offset from the center position C of the distal end portion main body 36.

Next, a positional relationship among the opening portion 58, the elevator housing portion 62, and the observation window 44 will be described. In the embodiment, as illustrated in FIG. 6, as the elevator housing portion 62 is provided on the lower side in the distal end portion main body 36, the positional relationship among the respective components configuring the distal end portion main body 36 can be set as follows.

As illustrated in FIG. 4, a position of the observation window 44 in the first direction (the up-and-down direction of FIG. 4) shown with the arrow A is disposed above the opening portion 58. That is, when a position of the opening portion 58 is set as a reference position, an axis 45 of the observation window 44 extended from a center position of the observation window 44 in parallel with the axis 38 of the distal end portion main body 36 is disposed above the reference position. As described above, as the observation window 44 is above the opening portion 58, the treatment tool can be put into an observation field of view of the observation window 44 at the position where the treatment tool is led out from the opening portion 58. Therefore, the treatment tool can be guided to a target position, and thus precision can be improved.

As for positions of the observation window 44 and the elevator housing portion 62 in the second direction, it is preferable to dispose the observation window 44 to be offset from the elevator housing portion 62 in the second direction shown with the arrow B, as illustrated in FIG. 3. Herein, disposing the observation window 44 to be offset from the elevator housing portion 62 in the second direction means that, for example, as illustrated in FIG. 3, when seen from above, a center line 44A of the observation window 44 is shifted from a center line 60A of the elevator 60 in the second direction shown with the arrow B. With such a configuration, even in a case where the elevator 60 is elevated and the treatment tool is led out from the opening portion 58, the observation field of view of the observation window 44 can be prevented from being blocked by the treatment tool and the elevator 60, and thereby the treatment position can be reliably checked through the observation window 44.

Figure 7:
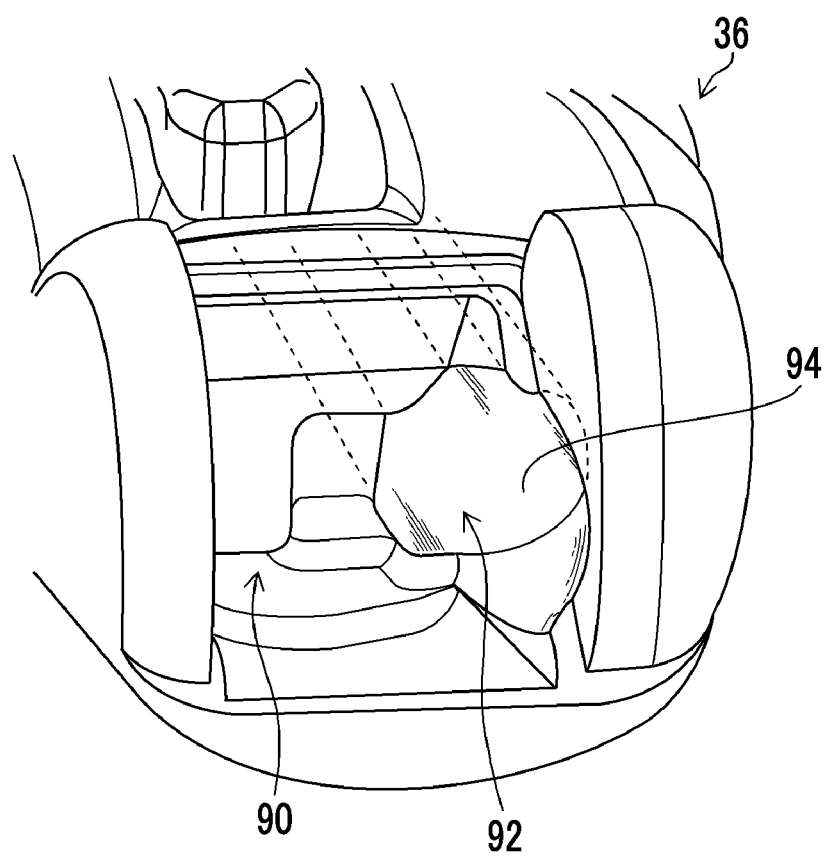
FIG. 7 is a perspective view of a distal end portion main body in a state where an ultrasonic transducer is removed.
Figure 8:
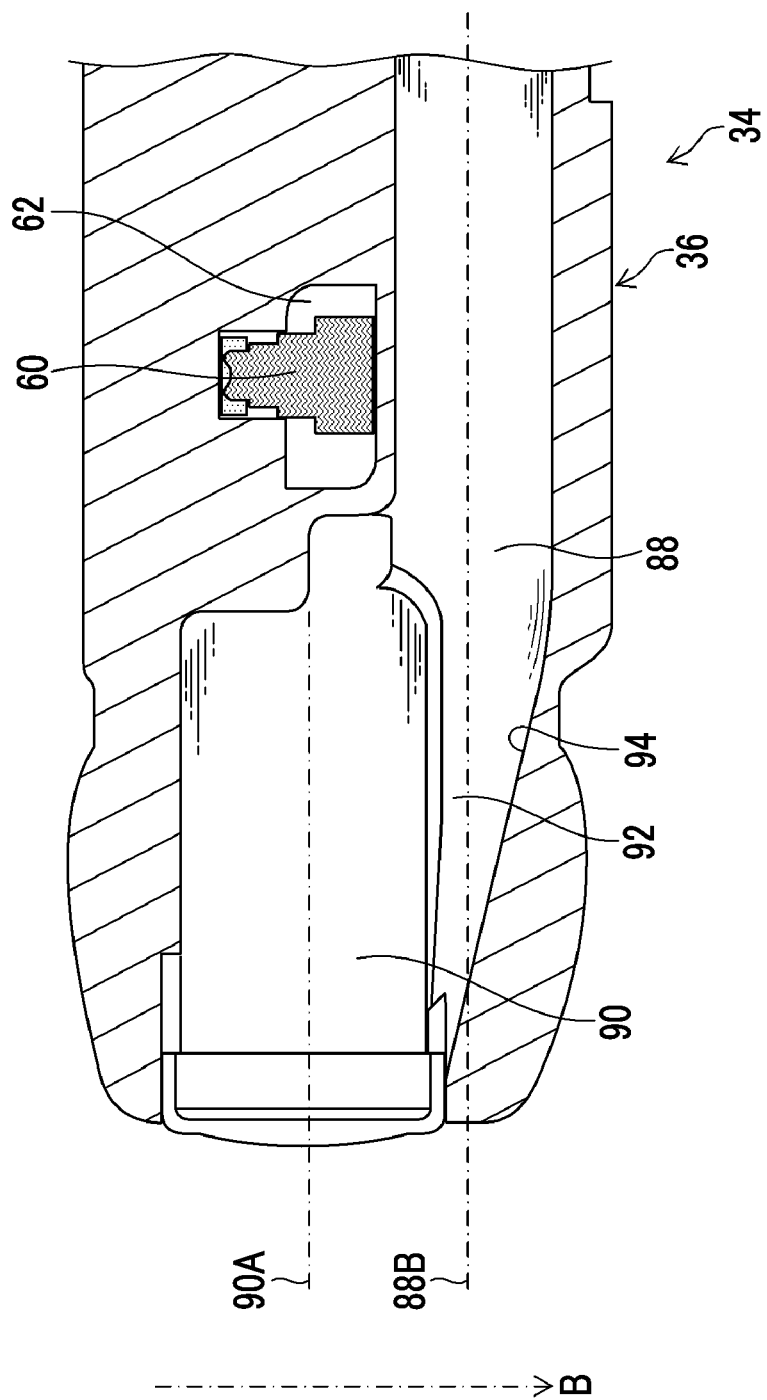
FIG. 8 is a cross-sectional view of an upper surface of the distal end portion main body.

FIG. 7 is a perspective view of the distal end portion main body 36 in a state where the ultrasonic transducer 50 is removed. FIG. 8 is a cross-sectional view of an upper surface of the distal end portion main body 36. A storing portion 90 that stores the ultrasonic transducer 50 is comprised on the distal end side in the direction of the axis 38 of the distal end portion main body 36. The cable insertion hole 88 is disposed at a position shifted from the storing portion 90 in the second direction. That is, the storing portion 90 is disposed at a position offset in the second direction from a position where the cable insertion hole 88 is provided. Herein, disposing the storing portion 90 at the position offset from the position where the cable insertion hole 88 is provided means that, for example, as illustrated in FIG. 8, when seen from above, a center line 90A of the storing portion 90 is shifted from a center line 88B of the cable insertion hole 88 in the second direction shown with the arrow B.

In addition, the storing portion 90 comprises a cable introducing portion 92 that introduces the plurality of signal cables 86 connected to the ultrasonic transducer 50 into the cable insertion hole 88. The cable introducing portion 92 is provided in the storing portion 90 to extend to a cable insertion hole 88 side in the second direction. Out of surfaces configuring the storing portion 90, which face the second direction, a surface on the cable insertion hole 88 side is formed by a guiding surface 94. The guiding surface 94 is formed such that a width of the storing portion 90 in the second direction gradually increases toward the proximal end side in the direction of the axis 38 of the distal end portion main body 36. The signal cable 86 is disposed along the guiding surface 94 and is introduced into the cable insertion hole 88. In FIG. 8, the guiding surface 94 is configured as an inclined surface that is inclined obliquely in a direction in which the width of the storing portion 90 increases from the distal end side to the proximal end side of the distal end portion main body 36. In addition, in a case where cross-sectional shapes of a connecting portion between the cable introducing portion 92 and the cable insertion hole 88 vary, the signal cable bends in some cases at the connecting portion between the cable insertion hole 88 and the cable introducing portion 92. Therefore, it is preferable that the cross-sectional shapes of the connecting portion between the cable insertion hole 88 and the cable introducing portion 92 are the same.

Figure 9:
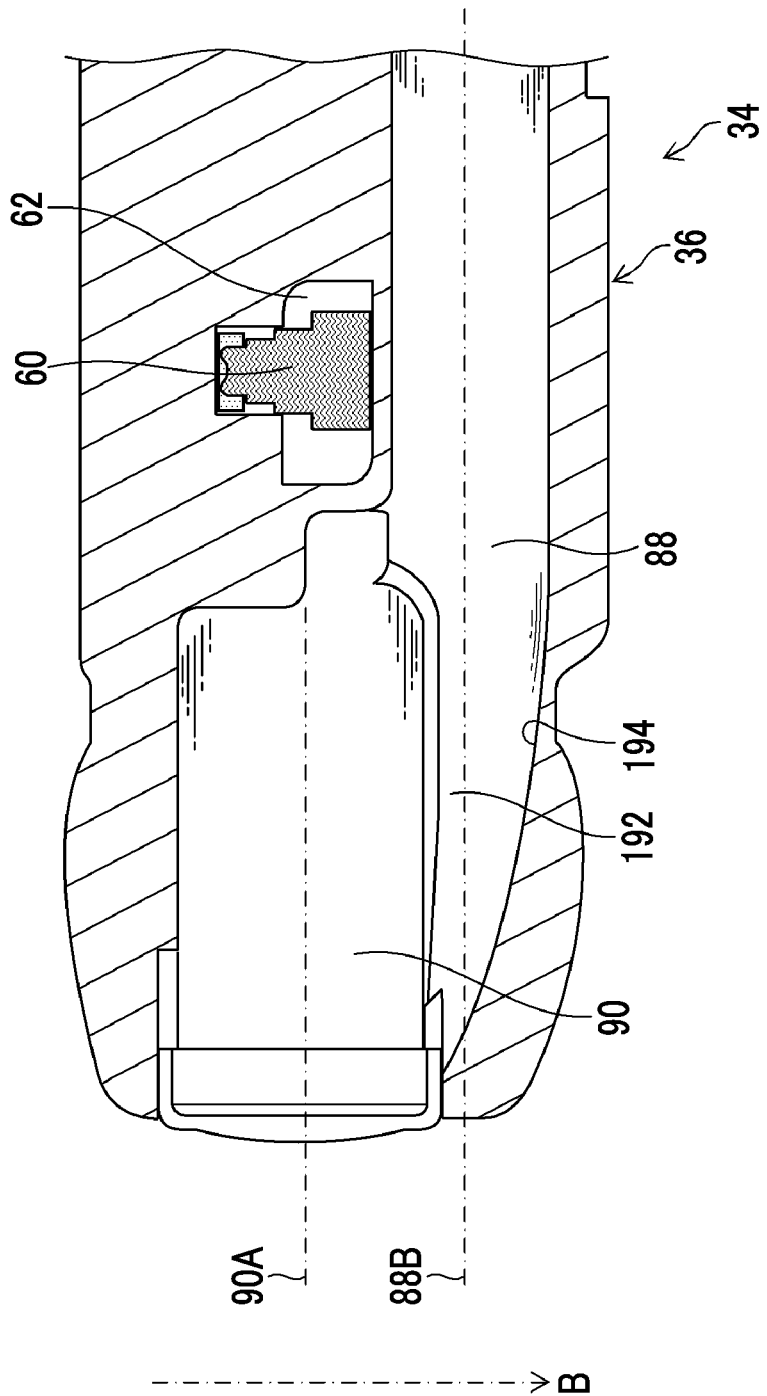
FIG. 9 is a cross-sectional view of an upper surface illustrating another embodiment of a guiding surface.

FIG. 9 is a view illustrating another embodiment of the guiding surface. As illustrated in FIG. 9, a cable introducing portion 192 can also be configured by forming a guiding surface 194 with a curved surface and forming the guiding surface to extend in the second direction to the proximal end side of the distal end portion main body 36. In FIGS. 8 and 9, some members are omitted.

As the guiding surfaces 94 and 194 are configured to be widened in a width direction of the cable introducing portions 92 and 192 as going toward the proximal end side of the distal end portion main body 36 and the signal cable 86 is introduced into the cable insertion hole 88 along the guiding surfaces 94 and 194, the signal cable can be prevented from abruptly bending, and the signal cable can be prevented from being disconnected.

Figure 10:
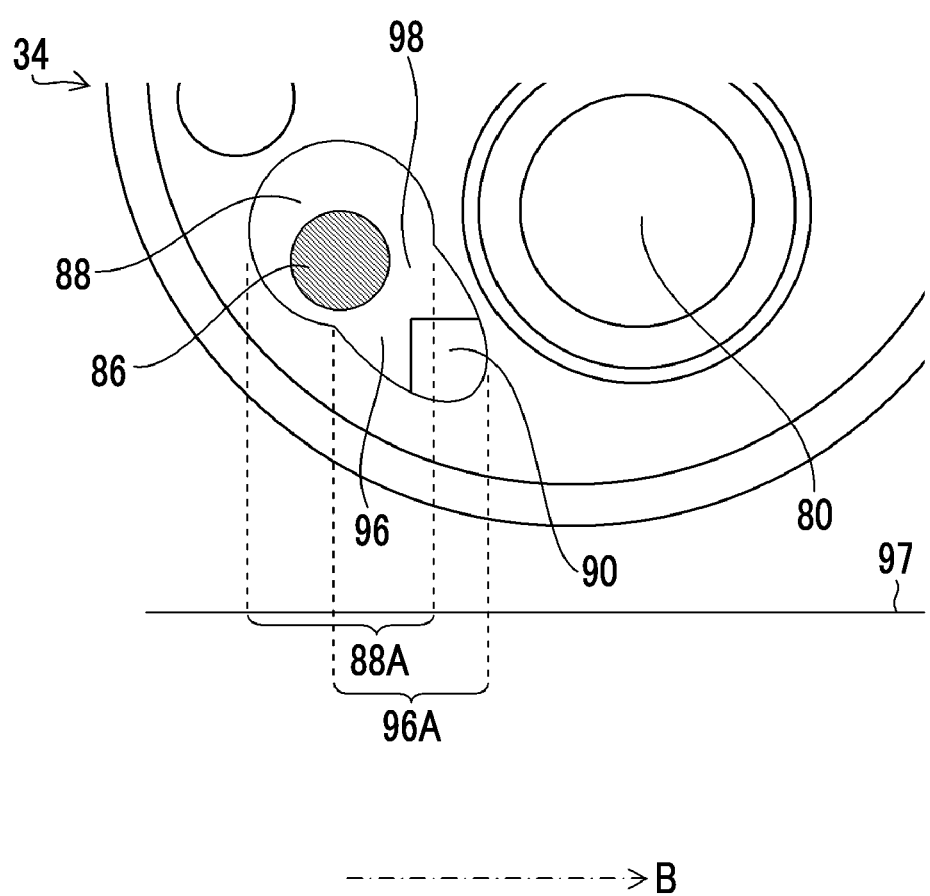
FIG. 10 is a partially enlarged view of a cross section in a case where the distal end portion main body is seen from a proximal end side.

FIG. 10 is a partially enlarged view illustrating the cable insertion hole 88 in a case where the distal end portion main body 36 is seen from the proximal end side. The distal end portion main body 36 has a needle insertion hole 96 for guiding a needle for injecting a filler to the storing portion 90. The signal cable 86 is fixed to the distal end portion main body 36 with the filler. As the needle is inserted from the proximal end side of the distal end portion main body 36 and the filler is injected from the distal end side of the distal end portion main body 36, the storing portion can be filled with the filler while drawing out air existing in the storing portion 90 from the proximal end side of the distal end portion main body 36, and the storing portion can be sealed with the filler without air bubbles mixed.

When a position of the needle insertion hole 96 of the distal end portion main body 36 in the second direction is projected on an imaginary plane 97 (that is, a plane parallel to the second direction) orthogonal to the axial direction of the distal end portion main body 36, it is preferable that a region 96A of the needle insertion hole 96 is disposed at a position closer to the storing portion 90 than the region 88A of the cable insertion hole 88 is. As illustrated in FIG. 8, the guiding surface 94 configuring the cable introducing portion 92 is formed in the direction where the width of the storing portion 90 increases from the distal end side to the proximal end side of the distal end portion main body 36. Therefore, as the needle insertion hole 96 is formed on a storing portion 90 side of the cable insertion hole 88 in the second direction, a distal end of the needle can be inserted to the distal end side of the distal end portion main body 36. Accordingly, the storing portion 90 can be easily filled with the filler from the distal end side.

In addition, it is preferable that the cable insertion hole 88 and the needle insertion hole 96 communicate with each other via a gap 98 along the axial direction of the distal end portion main body 36. As the cable insertion hole 88 and the needle insertion hole 96 are allowed to communicate with each other via the gap 98, the filler can be simultaneously injected into the cable insertion hole 88 and the needle insertion hole 96.

<Manufacturing Method of Ultrasonic Endoscope>

Figure 11:
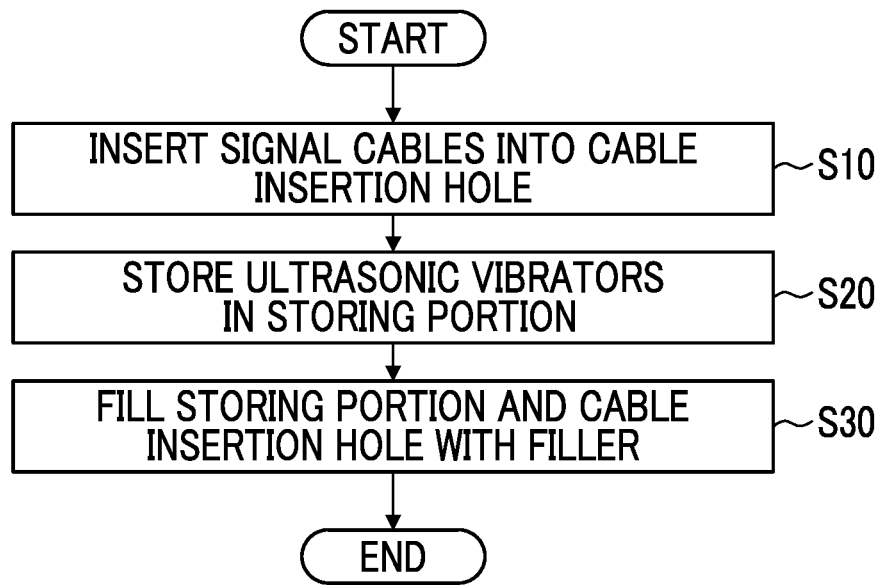
FIG. 11 is a flowchart showing a manufacturing method of an ultrasonic endoscope.

Next, the manufacturing method of an ultrasonic endoscope will be described. FIG. 11 is a flowchart showing a manufacturing method of the ultrasonic endoscope 1 according to the embodiment. FIGS. 12 to 18 are views illustrating the manufacturing method of an ultrasonic endoscope. The manufacturing method of an ultrasonic endoscope of the embodiment has Step (S10) of inserting the plurality of signal cables into the cable insertion hole, Step (S20) of storing the plurality of ultrasonic vibrators in the storing portion, and Step (S30) of filling the storing portion and the cable insertion hole with a filler.

Figure 12:
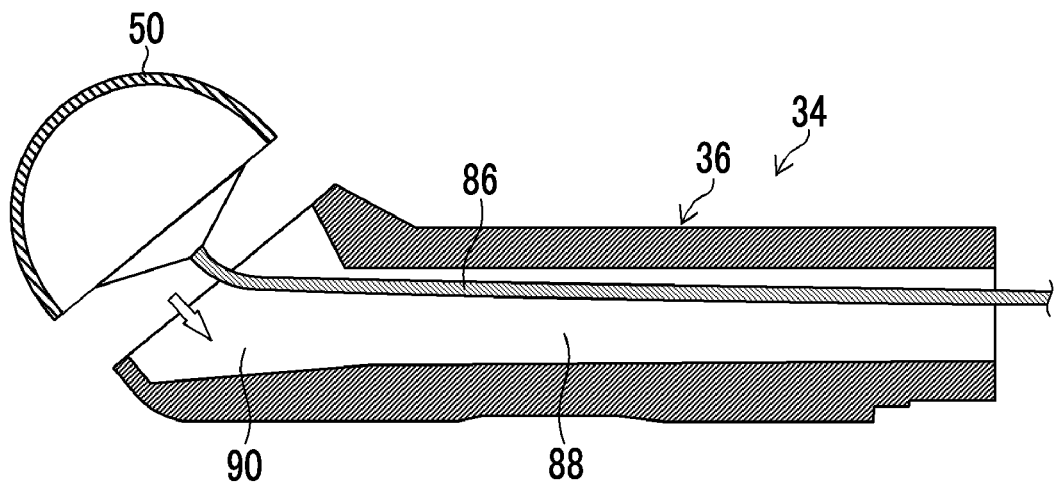
FIG. 12 is a view illustrating the manufacturing method of an ultrasonic endoscope.
Figure 13:
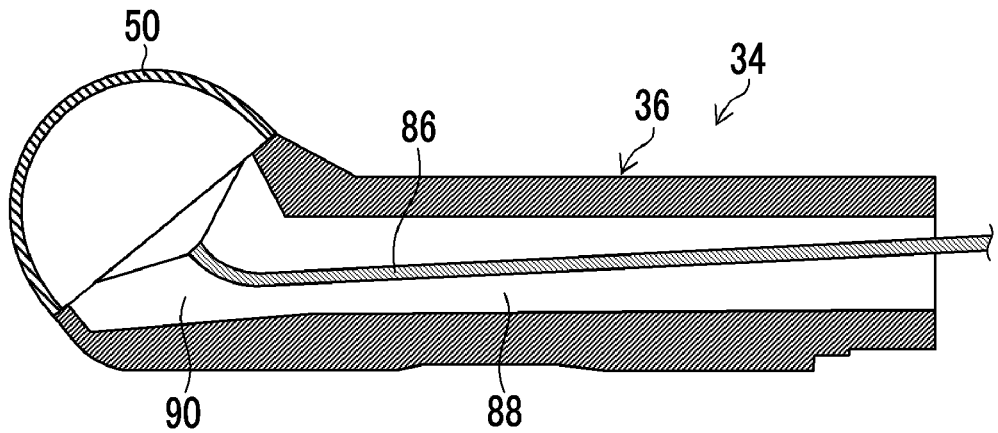
FIG. 13 is a view illustrating the manufacturing method of an ultrasonic endoscope.

Specifically, first, as illustrated in FIG. 12, the signal cable 86 connected to the ultrasonic transducer 50 is inserted into the cable insertion hole 88 of the distal end portion main body 36. The signal cable 86 is inserted from the storing portion 90 side, which is the distal end side of the distal end portion main body 36, and is inserted to the proximal end side of the distal end portion main body 36. In this case, as the signal cable 86 is introduced along the guiding surface 94 of the cable introducing portion 92 illustrated in FIG. 8, the signal cable 86 can be smoothly introduced into the cable insertion hole 88 (S10). Next, as illustrated in FIG. 13, the ultrasonic transducer 50 is stored in the storing portion 90 (S20). After storing the ultrasonic transducer 50 in the storing portion 90, a filler is injected into gaps of the storing portion 90 and the cable insertion hole 88, and the ultrasonic transducer 50 and the signal cable 86 are fixed to the distal end portion main body 36 (S30). Since the signal cable 86 is introduced into the cable insertion hole along the guiding surface 94 as described above, the signal cable 86 can be disposed in the distal end portion main body 36 without the signal cable 86 being bent abruptly and disconnected.

Figure 14:
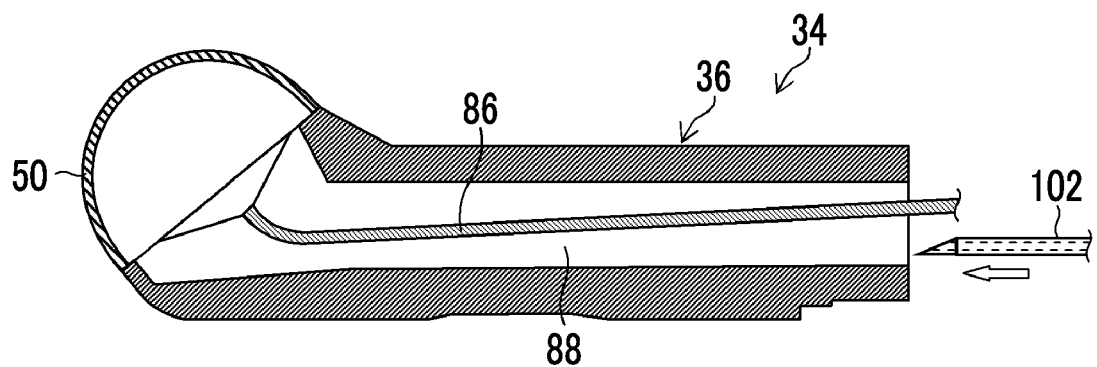
FIG. 14 is a view illustrating a filler injecting method.
Figure 15:
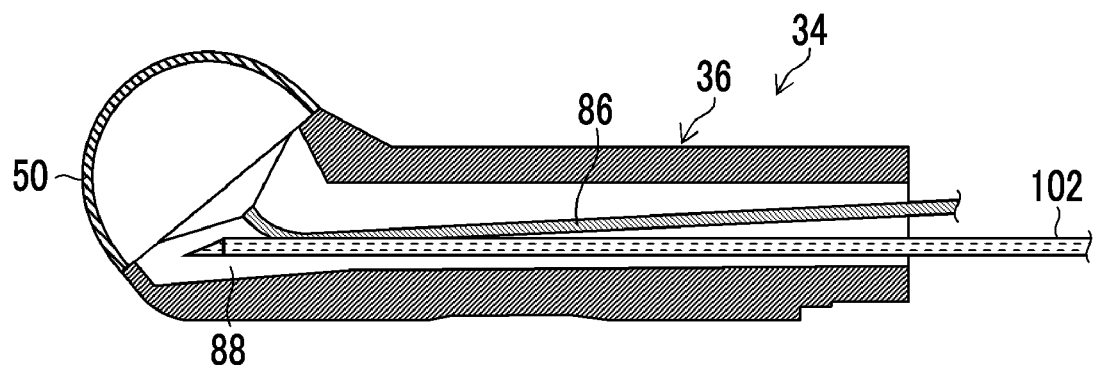
FIG. 15 is a view illustrating the filler injecting method.
Figure 16:
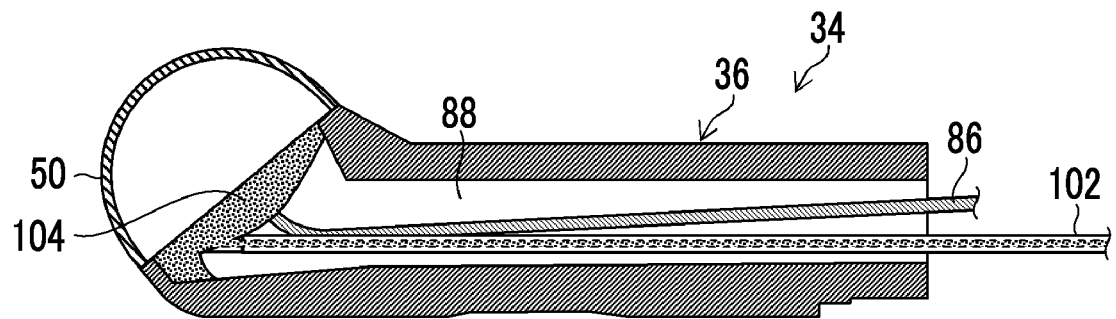
FIG. 16 is a view illustrating the filler injecting method.
Figure 17:
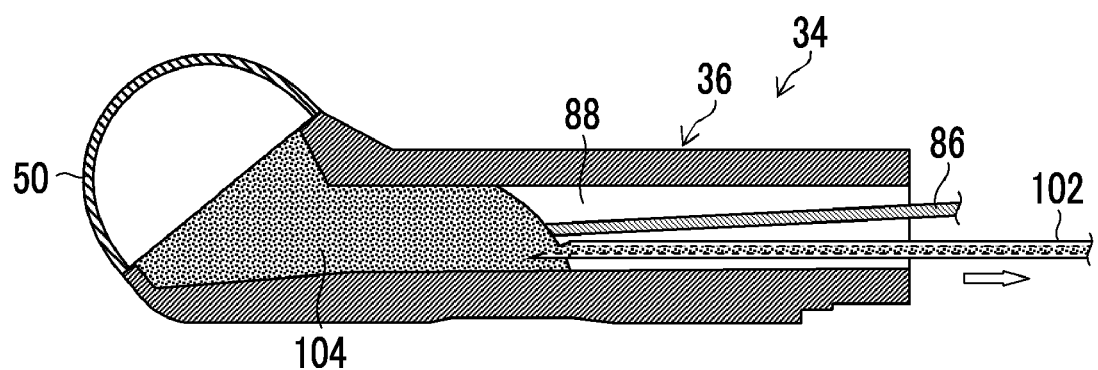
FIG. 17 is a view illustrating the filler injecting method.
Figure 18:
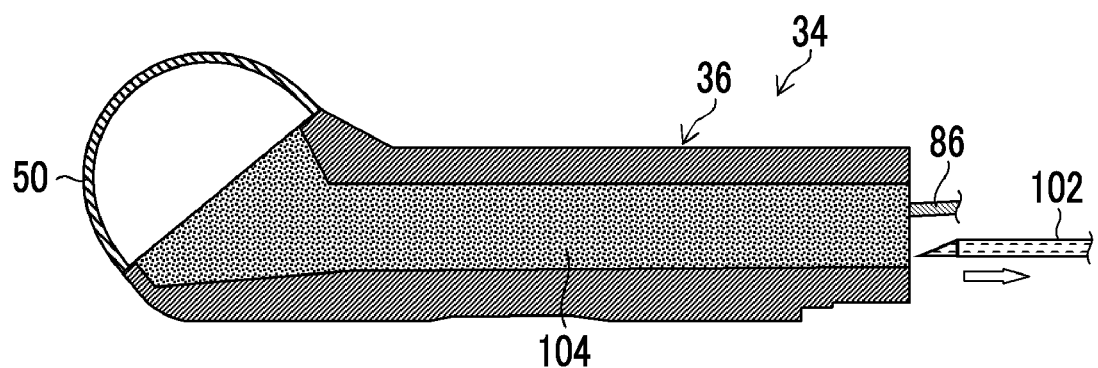
FIG. 18 is a view illustrating the filler injecting method.

A filler injecting method will be described with reference to FIGS. 14 to 18. To inject a filler, first, a needle 102 for injecting the filler is inserted from the proximal end side to the distal end side of the distal end portion main body 36 (FIGS. 14 and 15). After the needle 102 is inserted to a distal end of the distal end portion main body 36, a filler 104 is injected (FIG. 16). As the filler 104 is injected while pulling the needle 102 to the proximal end side of the distal end portion main body 36 (FIG. 17), a gas in the storing portion 90 and the cable insertion hole 88 can be discharged from the proximal end side of the distal end portion main body 36. Thus, air bubbles can be prevented from being mixed into the filler 104. By pulling out the needle 102 from the proximal end side of the distal end portion main body 36, the gap between the cable insertion hole 88 and the needle insertion hole 96 is filled with the filler.

Accordingly, since the gap can be filled with the filler in a state where the signal cable 86 connected to the ultrasonic transducer 50 is smoothly introduced into the cable insertion hole 88, the bending of the signal cable 86 can be alleviated, and the signal cable 86 can be prevented from being disconnected. In addition, since the signal cable 86 can be smoothly introduced into the cable insertion hole along the guiding surface 94, the assemblability of the ultrasonic transducer 50 into the distal end portion main body 36 can be improved.

As described above, in the embodiment, since the cable introducing portion 92 is included in the storing portion 90 storing the ultrasonic transducer 50 and the cable introducing portion 92 has the guiding surface 94 in the direction in which the width of the storing portion 90 in the second direction gradually increases from the distal end to the proximal end side, the signal cable can be prevented from being disconnected as the signal cable 86 is introduced into the cable insertion hole 88 along the guiding surface 94.

EXPLANATION OF REFERENCES

1: ultrasonic endoscope
10: operation part
12: insertion part
14: universal cord
16: angle knob
18: elevating operation lever
20: air supply and water supply button
22: suction button
24: treatment tool inlet
30: flexible portion
32: curving portion
34: distal end portion
36: distal end portion main body
38: axis of distal end portion main body
40: base portion
42: extension portion
44: observation window
44A: center line of observation window
45: axis of observation window
46L, 46R: illumination window
48: air supply and water supply nozzle
50: ultrasonic transducer
52: ultrasonic wave transmitting and receiving surface
58: opening portion
60: elevator
60A: center line of elevator
60a: guide surface
62, 62A: elevator housing portion
68: standing wall portion
72: observation means forming surface
80: treatment tool outlet
82: treatment tool insertion channel
86: signal cable
87, 97: imaginary plane
88, 88A: cable insertion hole
88B: center line of cable insertion hole
90: storing portion
90A: center line of storing portion
92, 192: cable introducing portion
94, 194: guiding surface
96: needle insertion hole
98: gap
102: needle
104: filler

What is claimed is:

1. An ultrasonic endoscope comprising:
a distal end portion main body that is provided at a distal end of an insertion part and has a cable insertion hole therein;
a storing portion that is provided in the distal end portion main body and is formed on a distal end side in an axial direction of the distal end portion main body from the cable insertion hole;
an ultrasonic transducer that is disposed in the storing portion and has a plurality of ultrasonic vibrators;
an elevator housing portion that is provided in the distal end portion main body and is open in a first direction orthogonal to the axial direction of the distal end portion main body;
an elevator that is provided in the elevator housing portion;
a plurality of signal cables that are connected to the plurality of ultrasonic vibrators, respectively; and
a cable introducing portion, communicating with the storing portion and the cable insertion hole, and introduces the plurality of signal cables to the cable insertion hole,
wherein the storing portion is disposed at a position offset in a second direction, which is orthogonal to the axial direction of the distal end portion main body and is orthogonal to the first direction, from a position where the cable insertion hole is provided,
an inner wall surface of the cable introducing portion has a guiding surface communicating with the cable insertion hole, in which a width of the guiding surface in the second direction increases from the storing portion toward a proximal end side in the axial direction of the distal end portion main body.

2. The ultrasonic endoscope according to claim 1, wherein the guiding surface is formed by an inclined surface which is obliquely inclined with respect to the axial direction of the distal end portion main body.

3. The ultrasonic endoscope according to claim 1, wherein when the cable insertion hole and the elevator housing portion are projected on a plane perpendicular to the first direction, the cable insertion hole is disposed in a region different from the elevator housing portion.

4. The ultrasonic endoscope according to claim 1, wherein when the distal end portion main body is projected on a plane orthogonal to the axial direction of the distal end portion main body, the distal end portion main body has an observation window of which a position in the first direction is disposed on an opening side of the elevator housing portion.

5. The ultrasonic endoscope according to claim 4, wherein the observation window is disposed on the proximal end side in the axial direction of the distal end portion main body from the elevator housing portion.

6. The ultrasonic endoscope according to claim 4, wherein the observation window is disposed to be offset from the elevator housing portion in the second direction.

7. The ultrasonic endoscope according to claim 1, wherein the storing portion is sealed with a filler without air bubbles.

8. The ultrasonic endoscope according to claim 1, wherein a filler is injected into gaps between the storing portion and the cable insertion hole.

9. The ultrasonic endoscope according to claim 1, wherein the guiding surface is formed with a curved surface.

10. The ultrasonic endoscope according to claim 1,
wherein in the distal end portion main body, a gap between the plurality of ultrasonic vibrators and the storing portion is filled with a filler.

11. The ultrasonic endoscope according to claim 10,
wherein the distal end portion main body has a needle insertion hole that guides a needle, which is for injecting the filler, to the storing portion.

12. The ultrasonic endoscope according to claim 11,
wherein when the needle insertion hole is projected on a plane orthogonal to the axial direction of the distal end portion main body, the needle insertion hole is disposed at a position closer to the storing portion than the cable insertion hole is.

13. The ultrasonic endoscope according to claim 12,
wherein the needle insertion hole and the cable insertion hole communicate with each other via a gap.

* * * * *